United States Patent [19]

Roberts

[11] Patent Number: 4,537,575
[45] Date of Patent: Aug. 27, 1985

[54] DENTURE SUPPORT FRAME

[76] Inventor: Harold D. Roberts, 202-1862 W. Broadway, Vancouver, BC, Canada, V6J 1Y9

[21] Appl. No.: 684,151

[22] Filed: Dec. 19, 1984

Related U.S. Application Data

[63] Continuation of Ser. No. 527,237, Aug. 29, 1983, abandoned.

[51] Int. Cl.³ .............................................. A61C 8/00
[52] U.S. Cl. .................................................. 433/176
[58] Field of Search ................................. 433/173, 176

[56] References Cited

U.S. PATENT DOCUMENTS

| | | | |
|---|---|---|---|
| 2,002,048 | 5/1935 | Thomas | 433/172 |
| 3,577,853 | 5/1971 | Roberts | 433/176 |
| 3,641,671 | 2/1972 | Roberts | 433/176 |
| 3,738,004 | 6/1973 | Edelman | 433/176 |
| 3,889,375 | 6/1975 | Roberts | 433/176 |
| 3,908,269 | 9/1975 | Christenot | 433/176 |
| 4,062,119 | 12/1977 | Linkow | 433/176 |
| 4,202,099 | 5/1980 | Roberts | 433/176 |
| 4,377,382 | 3/1983 | Roberts | 433/176 |

Primary Examiner—John J. Wilson
Attorney, Agent, or Firm—Eugene M. Eckelman

[57] ABSTRACT

A one-piece U-shaped bar is arranged to support an artificial denture on its upper edge. The front of the bar is curved and the side portions thereof are substantially straight whereby to be of a contour similar to the contour of the lower jaw of a person. The bar has rear ramus implant portions as well as a front implant portion. Each of the ramus implant portions extends upwardly at an angle greater than a right angle but less than 180° relative to the bar and also comprises an extention of the sides of the bar. Except for a small outward bend of the bar at the sides immediately forward of the ramus implant portions, the latter are substantially in longitudinal alignment with such sides. The ramus implant portions project upwardly as well as downwardly relative to the bar, with the upwardly extending portion having a length substantially greater than the downwardly extending portion. These upwardly and downwardly extending portions are pointed at their ends.

2 Claims, 4 Drawing Figures

U.S. Patent     Aug. 27, 1985     4,537,575

DENTURE SUPPORT FRAME

This application is a continuation of application Ser. No. 527,237, filed Aug. 29, 1983, and now abandoned.

BACKGROUND OF THE INVENTION

This invention relates to new and useful improvements in denture support frames of the type which include implants set in the jaw bone.

Various types of implants have been conceived for anchoring artificial dentures to the jaw bones. A basic implant, as shown in my U.S. Pat. No. 3,577,853, comprises a body member arranged to be mounted in the ramus portion of the lower mandible and including an integral post extending up from one end of the body member. This post protrudes above the bone and through the gum tissue to provide a denture support. From such ramus implants, dental supports have expanded in their concept to include bar members leading fully around the lower mandible between the ramus portions of the mandible. Examples of such bars are shown in my U.S. Pat. No. 3,641,671 and in U.S. Pat. No. 4,377,382. In the formation of such bar-type denture supports, it is desired that the bar have a solid support in the ramus portions of the mandible and also that it have a structure which will not pivot in the bone or deflect to the extent that the implants will loosen in the bone due to the stresses of mastication. Such support can be inadequate if the bars are of improper shape and also if they fit improperly in the ramus portions.

It has generally been thought that the best securement of the ends of the bars to the ramus portions of the mandible is adjacent the outer surface of the mandible since this outer portion is made up of hard corticle type bone. In shaping the bar and end implant portions thereof, the denture support bars have been made with offset or reversing curvatures and the ramus implant portions severely angled to reach this hard corticle bone location. The shaping of the bar and end implant portions to provide this implant installation contributed to deflection which eventually caused the implant to loosen from the stresses of mastication. Such shaping of the bar also tended to locate the bar close to the sides of the mouth and has resulted in compaction of food in these areas.

SUMMARY OF THE INVENTION

According to the present invention and forming a primary objective thereof, a denture support frame is provided which overcomes deficiencies of prior devices in that the ramus implant portions have a shape and disposition on the bar such that a solid support is provided in the jaw bone and one which resists pivoting or deflecting due to the stresses of mastication. An objective is also achieved by the shape of the denture support bar for minimizing food compaction in side areas of the mouth.

In carrying out the main objectives of the invention, a one-piece U-shaped bar has upper and lower edges and is arranged to support an artificial denture on its upper edge. The bar has front and rear portions with the front being curved similar to the front curvature of the lower mandible and the rearwardly extending portions at the sides being substantially straight similar to the sides of the mandible, whereby in its over-all shape has a contour similar to the contour of the lower mandible of a person. A rear ramus implant portion is provided on each side and these portions are arranged to be implanted in recesses cut in the ramus portions of the mandible. Each of the ramus implant portions comprises a rear extension of the bar extending upwardly at an angle which is greater than a right angle to the bar but less than 180°. In addition, these ramus implant portions comprise longitudinal extensions of the bar and are disposed in substantially the same upright plane as the rear portions of the bar. The rear portions of the bar just forward of the ramus implant portions are turned outward a small amount whereby to be disposed out of alignment with the straight side portions of the bar. The ramus implant portions of the bar also extend downwardly relative to the point of connection with the bar, the upward extension having a length substantially greater than the downward extension. These extensions are tapered to a point for forceable entry into the bone if desired.

The invention will be better understood and additional objects and advantages will become apparent from the following description taken in connection with the accompanying drawings.

DETAILED DESCRIPTION OF A PREFERRED EMBODIMENT

Figure 3:
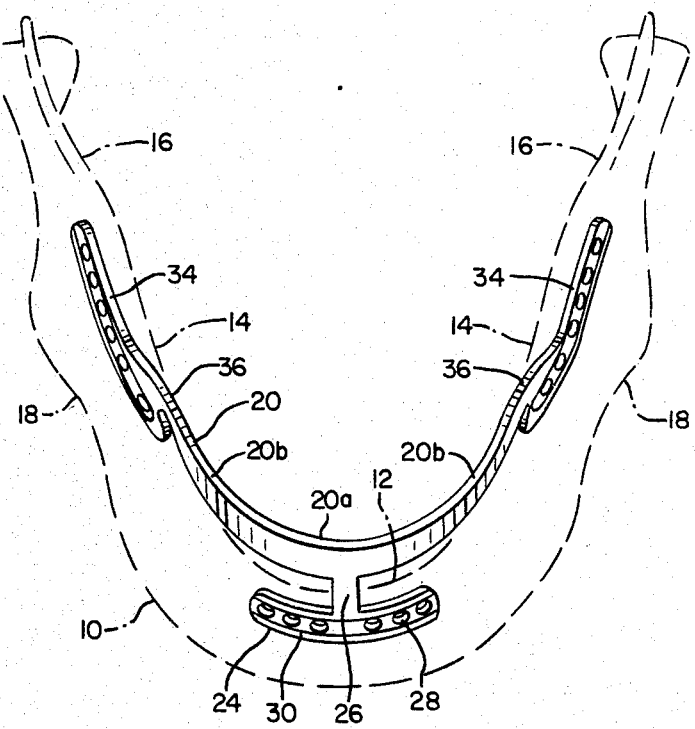
FIG. 3 is a top plan view of the denture support bar and mandible, the mandible being shown in broken lines.

With particular reference to the drawings, the numeral 10 designates a jaw bone or mandible of a person. As best seen in FIG. 3, the forward portion 12 of the mandible is curved and the sides 14 thereof extend from such curvature in almost a straight line to ramus portions 16. Ramus portions 16 comprise a rearward longitudinal extension of the mandible but also extend vertically for hinged connection to the skull. The lower rearward ends 18 of the ramus portions angle outwardly a slight amount to the rear and have substantially straight side surfaces. The surface portions of the mandible, including the ramus portions, consist of hard corticle-type bone and the interior thereof consists of spongy type bone.

The present invention is concerned with a rigid U-shaped denture support bar 20 which extends along the upper ridge of the lower mandible. As is customary in the use of this type of denture support frame, the natural teeth have all been removed and the bar 20 is arranged to support a full artificial denture 22 which is firmly but removably seated on the bar in a known manner into comfortable contact with or in close proximity to the gum surface. The gum surface is designated by the reference numeral 21 in FIG. 2. The present invention is used primarily on mandibles having severe damage or atrophy wherein surface support of dentures is not practical. As seen in FIG. 3, which shows a representative mandible, the front of the mandible is generally inclined rearwardly whereby a most efficient implant extending down through the upper ridge of this portion of the mandible must also be inclined in order to take advantage of uniform bone thickness and strength.

The denture support bar 20 is shaped from end to end to conform to the shape and size of the mandible so as to overlie the latter. That is, it has a curved front portion 20a similar to the curved portion 12 of the front of the mandible and it has substantially straight side portions 20b conforming to the substantially straight side portions 14 of the mandible. The bar is provided with an integral downwardly extending frontal implant blade 24 supported at the central forward portion by a depending post 26. The blade 24 has a plurality of holes 28 therein which allow for bone growth and also has concaved surface portions 30 to receive bone growth. This blade anchors the bar at the front. The supporting post 26 for the blade 24 angles forwardly a slight amount from the bar 14 and the blade 24 is fitted in a similarly angled recess 32 in the front portion of the mandible. This recess is cut to conform substantially to the angle of the mandible at the front with consideration given to damage or atrophy of the mandible to accomplish the best attachment to the bone.

Rear anchor points of the bar 20 comprise ramus implant portions 34 at the two free ends. These ramus implant portions consist of rearward extensions of the bar except that the bar is provided with small outward bends or angles 36 just forward of the ramus implant portions the latter comprising an extension of the angled portions 36 and thus being out of alignment with the straight side portions of the bar, for reasons to be described more fully hereinafter. The ramus implant portions 34 have a portion 34a thereof extending above the bar and a portion 34b extending below the bar. The angle 37 between the juncture of the upper edge of the bar and the implant portion 34a is greater than a right angle but less than 180°. Although dimensions may vary, it is found that the length of the ramus portions 34a can be about 8 to 10 millimeters and the portions 34b can be 5 or 6 millimeters. The bottom edge 38 from one end of the ramus implant portion to the other is generally rounded in substantially a common radius. The top edge 40 of the ramus implant portions 34a rearward of the juncture with the bar assumes a radius of curvature similar to that of the bottom edge 38. Both ends 42 of the implant portions 34 taper to a point.

To install the present denture support frame, the recess 24 at the front is suitably made and recesses 44 suitably made in the ramus portions of the mandible for receiving the implant portions 34. In practice, recesses 44 in the ramus portions 16 are cut to the length of the implant plus a short distance upwardly past the point of installation. After being laid in such recesses, forward shifting movement of the bar for fitting the front blade 24 in its angled recess 32 is accomplished by forcefully driving the pointed lower end 34b into the soft bone of the mandible. This will leave a space in the bone at the upper end of the implant portions 34a but such portions, being in soft bone, will heal quickly. The recesses 44 may, however, be cut to a length such that the shifting movements for installation can be made by forced movement also of the pointed ends at the rear into the bone.

Figure 4:
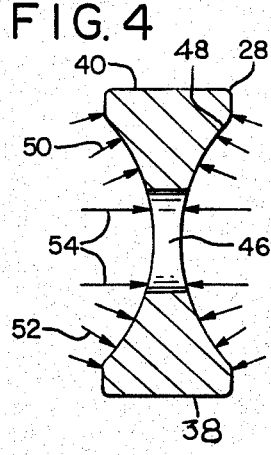
FIG. 4 is an enlarged sectional view taken on the line 4—4 of FIG. 1.

The ramus implant portions 34 with the bend 36 therein extend in their longitudinal dimension as extensions of the sides 20b of the bar 20 but out of alignment therewith. In such extension, these implant portions extend approximately toward frontal implant blade 24. This precise pointed direction of the ramus implant portions 34 not only provides a good fit interiorly of the ramus portions 16 of the mandible but also as the bar 20 is shifted forward to seat the frontal blade 24 in the recess 30 the forward movement of the implant portions 34 displaces a minimum amount of spongy bone. In this shifting movement, the forward end 34b is forcefully driven into the bone. Implant portions 34 have holes 46 therethrough and these implant portions as well as frontal blade 24 have concaved portions 48 on the sides through which the holes pass for good anchored support in the bone when the latter heals through the holes and into the concaved portions. FIG. 4 illustrates resisting forces of the implants 34 when installed, the front blade 24 accomplishing the same feature in that it has the holes 28 and is also concaved on its sides. That is, bone which is healing or which has healed around the implants resists occlusal forces at the concaved surface portions designated by the arrows 50 and resists elevating forces at the concaved surface portions designated by the arrows 52. The formed bone also resists lateral forces at the somewhat straight portions of the implants which is between the arrows 50 and 52 and which is designated by arrows 54. The implants are further firmly anchored by bone that heals through the apertures 46 . The flat bottom edge 38 provides a good support area in the bone to resist occlusal forces and the flat top edge 40 provides a good area to resist elevating forces. Frontal blade 24 similarly has the flat top and bottom edges.

Figure 1:
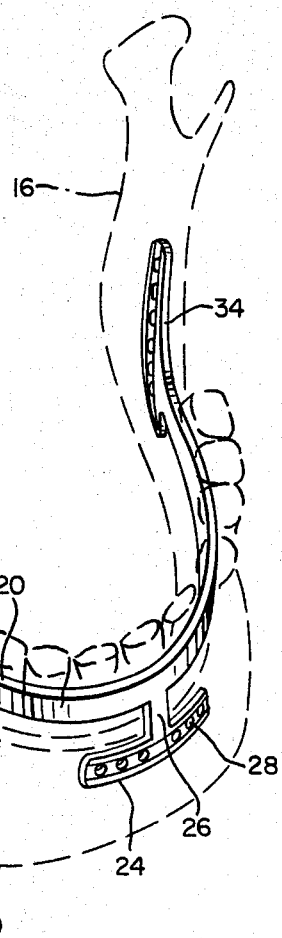
FIG. 1 is a perspective view of the present denture support frame, a mandible associated therewith being shown in broken lines.
Figure 2:
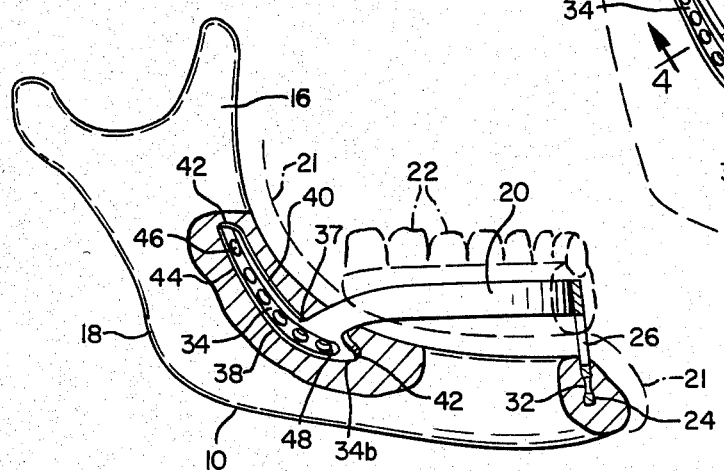
FIG. 2 is a side elevational view of a mandible with the present support frame installed therein, a portion of the mandible being broken away to show the implant portions installed therein.

With particular reference to FIG. 3, the bends 36 at the rear portions of the bar angle the implant portions 34 slightly outwardly. The recesses 44 for the implant portions 34 are cut in substantially a central area of the ramus portions 16 and the implant portions 34 in their offset disposition by the bends 36 extend down into the ramus portions at about the same angle that the ramus portion of the mandible extend. Although the bend 36 angles the ramus implant portions 34 at a preferred angle into the ramus portions of the mandible, the portions 34 are not out of alignment to an extent that would cause springiness in the bar. This provides a secured and strong locking engagement of the implant portions in the bone. With reference to FIG. 2, it is apparent that any stresses due to mastication in the molar area are directly downward on the implanted portions, and since the implant portions 34a are elongated and the portions 34b are of very short length, there is no pivot point around which stresses are applied within the ramus portions.

The recesses 44 of the implant portions 34 are of suitable depth so that the implant portions 34 are fully contained within the bone in order that there will be minimum chance of infection and minimum food impaction. The only protrusion at the ramus portions therefor will be the bar and the gum tissue will quickly heal around this bar so that also there will be minimum chance of infection and food compaction. Since the bar extends from the implant portions 34 at an angle greater than a right angle, food will not lodge in this angled point of penetration of the bar into the gum. Also, the shape of the bar 20 keeps the dentures a sufficient distance from the sides of the mouth to prevent food compaction at such sides of the mouth.

Another advantage of the particular shape and disposition of the implant portions 34 is that the surgeon can readily position burring tools to make the desired recesses.

It is to be understood that the form of my invention herein shown and described is to be taken as a preferred example of the same and that various changes in the shape, size and arrangement of parts may be resorted to without departing from the spirit of my invention, or the scope of the subjoined claims.

Having thus described my invention, I claim:

1. A denture support frame arranged to be secured to the lower jaw of a person for supporting an artificaial denture thereon, said frame comprising a one-piece U-shaped bar having upper and lower edges and arranged to support an artificial denture on its upper edge, said bar having front and rear portions with the front being narrowed and curved and the rearwardly extending portions at the sides diverging outwardly in substantially a straight line whereby to be of a contour similar to the contour of the lower jaw of a person, a rear ramus implant portion on each side at the rear portion arranged to be implanted in recesses cut in the ramus portion of the jaw bone, and front support means on said bar arranged for engagement with the jaw, said ramus implant portions comprising rear longitudinal extensions of said bar, said extensions having substantially the same vertical disposition as the rear portion of said bar from which it extends, said extensions being joined with said bar at an angle substantially greater than a right angle but less than 180 degrees and extending both upwardly and downwardly relative to rear portions of the bar with the upward extending portion having a length substantially greater than the downward extending portion, said rear portions of said bar immediately forward of said ramus implant extensions being bent upward a small amount whereby to be disposed out of alignment with the straight side portions of said bar and to extend into the ramus jaw portions approximately centrally between the sides, said extensions being directed from front to rear toward said front support means.

2. The denture support frame of claim 1 wherein said upward extending portion of said extension is approximately 8 to 10 mm in length and said downward extending portion is approximately 5 to 6 mm in length.

* * * * *